(12) United States Patent
Littell

(10) Patent No.: US 7,004,921 B2
(45) Date of Patent: Feb. 28, 2006

(54) MALE GENITAL PROTECTION DEVICE

(76) Inventor: Mark Alan Littell, 6730 E. Hermosa Vista Dr., Mesa, AZ (US) 85215

(*) Notice: Subject to any disclaimer, the term of this patent is extended or adjusted under 35 U.S.C. 154(b) by 133 days.

(21) Appl. No.: 10/629,043

(22) Filed: Jul. 28, 2003

(65) Prior Publication Data

US 2004/0092851 A1    May 13, 2004

Related U.S. Application Data

(60) Provisional application No. 60/398,994, filed on Jul. 27, 2002.

(51) Int. Cl.
*A61F 13/00* (2006.01)

(52) U.S. Cl. ....................................... 602/67

(58) Field of Classification Search .................. 602/27, 602/68–73; 128/89.1, 98.1, 105.1, 95.1, 128/96.1; 2/425
See application file for complete search history.

(56) References Cited

U.S. PATENT DOCUMENTS

| 4,043,329 | A | * | 8/1977 | DiMatteo | ..................... 128/846 |
| 5,479,942 | A | * | 1/1996 | DiMatteo | ..................... 128/846 |
| 6,319,219 | B1 | * | 11/2001 | Landi | .......................... 602/67 |

* cited by examiner

*Primary Examiner*—Henry Bennett
*Assistant Examiner*—Shumaya B. Ali
(74) *Attorney, Agent, or Firm*—Thomas J. Finn

(57) ABSTRACT

A male genital protection device configured to conform to the shape of the male genital anatomy, which provides the wearer with added comfort and protection.

5 Claims, 3 Drawing Sheets

MALE GENITAL PROTECTION DEVICE

RELATED APPLICATIONS

Figure 1:
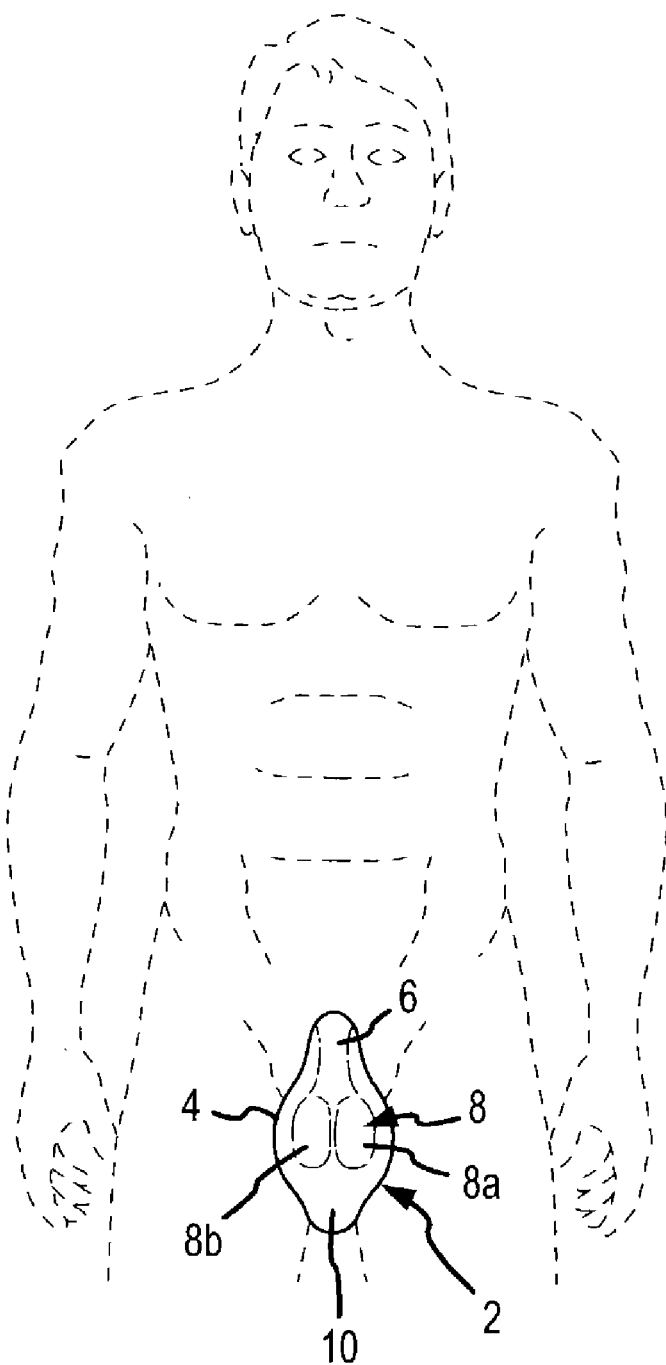

The present application claims the benefit of, and priority to, U.S. Provisional Ser. No. 60/398,994 filed Jul. 27, 2002, by Mark Littell entitled "Male Genital Protection Device," the entire contents of which are hereby incorporated by reference.

FIELD OF INVENTION

The present invention generally relates to an apparatus for protecting the male genitalia while providing a more comfortable and secure fitting. In particular, the genital protection device comprises conformed areas for securing the testicles and/or scrotum, the penis, and/or a flange positioned about the male crotch for stabilizing the device to prevent movement.

BACKGROUND OF THE INVENTION

Protective cups have been used for years by a variety of athletes, workers security personnel and the like. Traditionally, baseball players, hockey players, football players, and rugby players used protective cups to protect their male genitals from injury resulting from sporting contact or external impact. Recently, protective cups have become important in other sports such as mountain biking, motocross, snow skiing, waterskiing and the like. In describing traditional protective cups, it is important to understand the general physiology of the male anatomy as relating to a groin impact.

Because the testicles hang in a sac (i.e., scrotum) outside the body, they are not protected by bones and muscles like the rest of the reproductive system. The location of the testicles makes it easier for them to be injured or hit, a painful sensation most males have experienced. Generally, because the testicles are loosely attached to the body and are made of a spongy material, they are able to absorb the shock of impact without permanent damage. It is common, nonetheless, for males to experience testicular trauma, which is when the testicles are struck, hit, kicked, or crushed. Most testicular injuries of this sort occur during sports and can be very painful.

Another common type of testicular problem that occurs suddenly is called testicular torsion, and, although it is known to occur in males of all ages, it is particularly frequent in males between the ages of 12 and 18. It should be appreciated that within the scrotum, the testicles are secured at either end. Sometimes, a testicle can become twisted, cutting off the blood vessels that supply blood to the testicle. Testicular torsion occurs as the result of trauma to the testicles or as a result of strenuous activity. In the United States, testicular torsion occurs in one out of 4,000 males younger than 25. A more rare type of testicular trauma is called testicular rupture. This condition may occur when the testicle receives a direct blow or when the testicle is crushed by some object. The testicle is compressed against the pubic bone, crushing the testicle against the bone and the object, causing blood to leak into the scrotum.

The first type of protective cups developed, and still available, are the flat-profiled cups, which are not contoured and often do not have the necessary volume to provide any real protection. Traditional protective cup and similar devices include, for example, those described in U.S. Pat. Nos. 2,283,684; 3,314,422; 3,782,375; 4,453,541; 4,590,931; 5,479,942; 5,807,299; and 6,319,219, all of which are incorporated herein by reference. The more recent of the traditional cups are profiled and generally differ in two respects: the shape of the bottom end and the volume. For example, the traditional cups manufactured by Bike® and the Original Banana cups are pointed and relatively narrow; and the cups sold by Bauere®, Protex® and SafeTGard® are rounded at the bottom end and are relatively wide. These traditional devices have been primarily designed to absorb or divert the force of an impact from the genital region to the pelvic bone. In this regard, these devices have been relatively successfully in preventing testicular trauma as a result of a direct impact. However, the traditional cup design just described allows for a great deal of movement and jarring between testicles in the scrotum and the cup, between one testicle and the other, and between the testicles and the penis. Indeed, in some instances, depending on the particular male physiology, the traditional cup confines the testicles and penis in an open environment so as to increase the jarring activity, e.g., one testicle banging against the other. This jarring is enhanced during the performance of sporting or other physical activity—when a protective cup is most likely to be worn. During the course of fast moving sporting activity, the testicles shift within the cup and often shift place as the athlete moves quickly from one position to another. This confinement of the testicles in the open space of the traditional protective cup is believed to either increase the likelihood of testicle torsion or, at minimum, to not help prevent testicular torsion.

As those experienced in athletics can attest, the banging of one testicle against the other, or against the penis, or against the wall of a protective cup, results in a very discomforting, if not painful experience. As previously noted, this also may contribute to testicular torsion or even testicular rupture. The continuous jarring of the testicles causes minor discomfort at a minimum and has been known to cause at least temporary injury to the groin region.

The association of pain and discomfort with the wearing of the traditional protective cup has residual effects as well. For example, many do not wear a protective cup because of this discomfort associated therewith. These people are therefore much more susceptible to injury. Therefore, there is a currently unmet need in the protective device industry for a protective cup that not only provides protection from impact, but is more comfortable, easier to wear, and minimizes likelihood of testicular torsion.

SUMMARY OF THE INVENTION

This invention relates to a genital protection device that better conforms to the male genital anatomy to provide better comfort while maintaining a protective environment for the male genitals, thus overcoming the problems existing in the current state of the art of athletic cups. In particular, a preferred embodiment of this device includes a first and second portion, wherein the first portion has an elongated concave inner surface area extending from approximately the center of the device upward and the second portion has oval-shaped inner surface area. The first portion positions the penis in an upward direction and generally apart from the scrotum. The second portion conforms to the scrotum and preferably has two generally concave inner surface areas for separating and securing each of the two testicles. It is an objective of the present invention to minimize jarring of the testicles to aide in comfort for the user of the device. It is a further objective of this invention to provide reduce the likelihood of testicular trauma by providing a device that better conforms to the male genitals, thereby separating genitalia and minimizing possibility of testicular torsion and/or rupture.

DESCRIPTION OF THE INVENTION

The present invention is directed to a male genital protection device that is not a protective "cup" in the traditional sense because it is not necessarily a cup-shaped device. Rather, this device overcomes the problems of the traditional protective "cup" by generally conforming to and isolating the testicles and/or penis to prevent significant movement, thereby reducing the likelihood of, inter alia, (i) discomfort, (ii) testicular trauma, (iii) testicular torsion, and/or (iv) testicular rupture.

Figure 2:
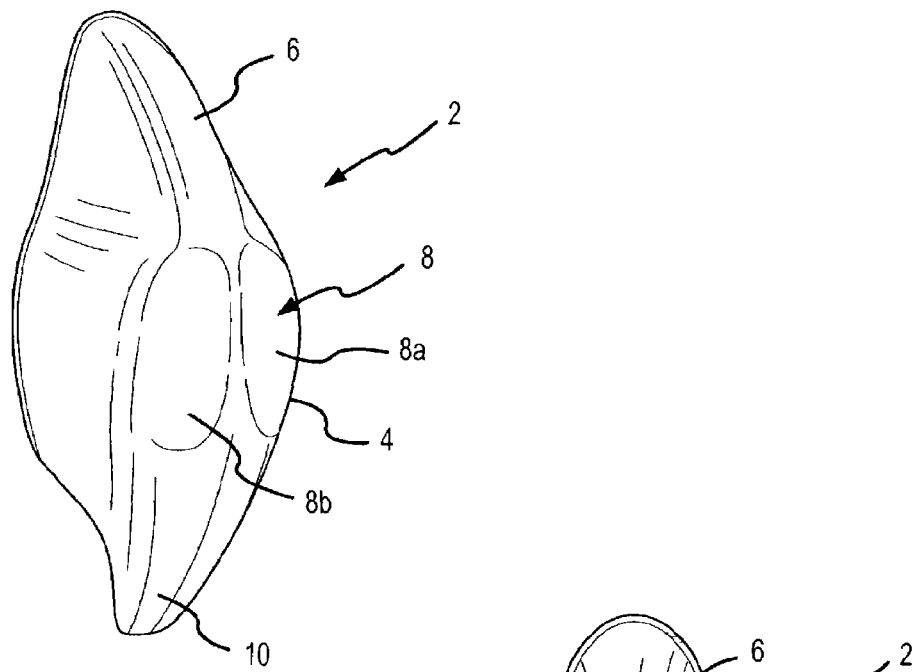
Figure 3:
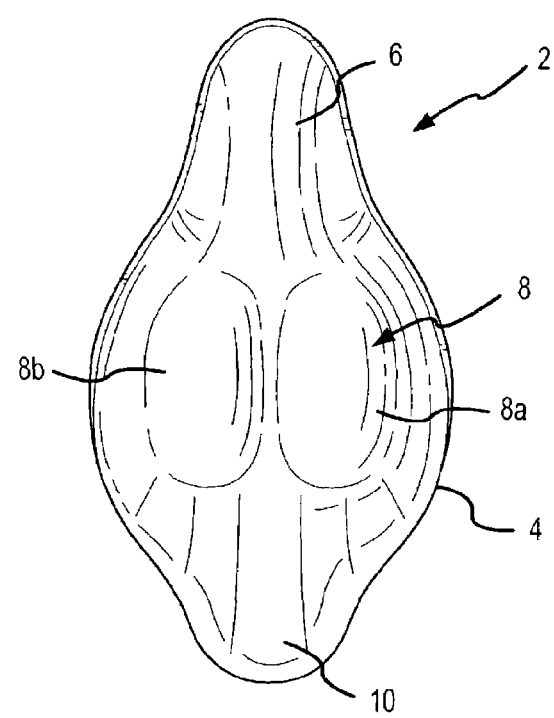
Figure 4:
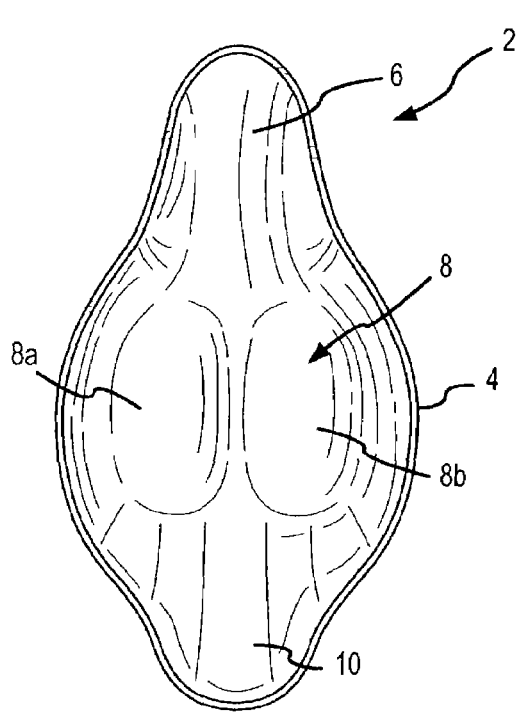
Figure 5:
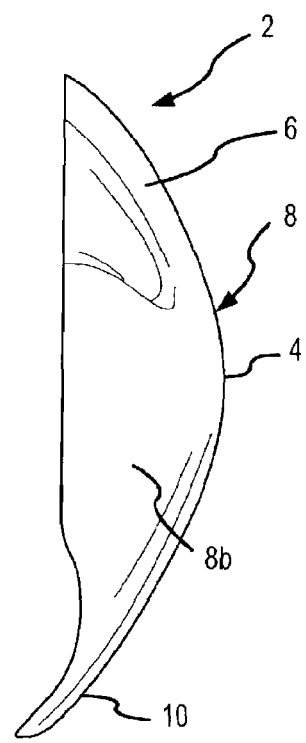

As such, a male genital protection device is described that is generally conformed to the male genitalia (i.e., male organs) to enhance comfort and increase protection. An exemplary embodiment of this device is depicted in FIGS. 1–5. As shown FIGS. 1–5, in an exemplary embodiment, a genital protection device 2 is formed with a first portion 6 configured to hold the penis in-place to prevent significant movement during exercise, sports or other activity. In addition, the genital protection device 2 may be formed with a second portion 8, which substantially secures the scrotum in place where each testicle may be generally separated, via conforming areas 8A and 8B, to further minimize jarring and other impact associated with wearing said device 2. The first portion 6 is preferably formed as a narrow, elongated concave inner-surface area that corresponds to the shape of the male penis. And, unlike prior art devices, when worn the first portion 6 of device 2 positions the penis pointed upward and generally against the body so as to held in a in a very natural position during physical activity. The second portion 8 preferably is separately contoured for each testicle, e.g., areas 8A and 8B. 8A and 8B are preferably configured horizontally and substantially next to each other, so each testicle is positioned horizontally during normal wear and activity. Of course, the device may be formed in various sizes and shapes to account for various ages and physiques.

In yet another embodiment or as an extension of the previously described embodiment, the device 2 may be configured with a flange 10 to reduce or minimize movement of the device 2 against the body and/or to provide a further separation from the body to absorb the shock of an impact. Flange 10 is positioned such that when device 2 is worn under normal conditions, the flange 10 helps to prevent lateral (i.e., horizontal x1-x2) or axial (i.e., vertical y1-y2) movement. This arrangement facilitates proper positioning such that on impact the force is diverted from the genital region to the pubic bone. In addition, the flange 10 may be formed of a more flexible material designed to collapse under forces applied to the device and/or during body movements. Other exemplary embodiments contemplated by the present invention include various combinations which may include only the penis portion 6, only the testicles/scrotum portion 4, the flange 10 or any combination of these. Depending on the sporting or athletic activity; or other protection desired, the protective device 2 may be suitably conformed to isolate various regions.

The device may be formed of any material of sufficient rigidity and durability to absorb and divert external impact forces. Examples of suitable materials include various hard plastics, polypropylene, HDPE, ABS, PC/ABS, PBT, and/or the like that may be extruded, vacuumed formed, molded, or formed by any suitable process. In addition, it may be desirable to have ventilating holes in the protective device 2. Furthermore, it is also contemplated that padding (e.g., foam, rubber, etc.) may be used for additional comfort. For security and military applications, the material used may be Kevlar or other harder materials.

It should be appreciated that the particular implementations shown and described herein are illustrative of the invention and its best mode and are not intended to otherwise limit the scope of the present invention in any way. Indeed, for the sake of brevity, conventional athletic cup materials, composites, ventilation and the like, which are known in the art, have not been described in detail herein. It should be appreciated, however, that a genital protection device configured with Kevlar or other similarly resilient material is also contemplated for use in military, police and/or other hazardous settings. It is also contemplated that the interior of the device may be configured so as to be conformed to the genitals whereas the exterior may take a traditional shape. Furthermore, it is also contemplated that the exterior surface may comprise a suitable material resistant to impact, while the interior surface may comprise a more cushioned or softer material.

I claim:

1. A male genital protective device comprising:
an elongated first portion shaped to hold a penis; and
a second oval portion shaped to conform to testicles within a male scrotum to minimize jarring of the testicles.

2. The protective device of claim 1 further comprising a flange positioned at the bottom of said second portion which facilitates securing the protective device to the male body to minimize horizontal and vertical movement.

3. A male genital protective device comprising:
an elongated first portion shaped to hold a penis; and
a second portion shaped to conform to a male scrotum, wherein said second portion is formed into two separate portions for containing the left and right testicles.

4. The protective device of claim 3, wherein said two separate portions are formed horizontally for securing said left and right testicles in a horizontal porition.

5. A male genital protective device providing increased comfort for a wearer and configured for positioning the male penis in an upward position against the human body and the testicles in a horizontal position below the penis wherein said device is comprised of a rigid material capable of withstanding a blunt force blow and absorbing and diverting the impact of said blow away from the genital area to the pubic bone region; and two separate oval portions for containing left and right testicles.

* * * * *